(12) United States Patent
Cai et al.

(10) Patent No.: US 9,213,407 B2
(45) Date of Patent: Dec. 15, 2015

(54) RING ACCESSORY

(71) Applicants: Charles Cai, Mather, CA (US); Scott Fritz, San Jose, CA (US); Esat Yilmaz, Santa Cruz, CA (US)

(72) Inventors: Charles Cai, Mather, CA (US); Scott Fritz, San Jose, CA (US); Esat Yilmaz, Santa Cruz, CA (US)

(73) Assignee: Atmel Corporation, San Jose, CA (US)

( * ) Notice: Subject to any disclaimer, the term of this patent is extended or adjusted under 35 U.S.C. 154(b) by 268 days.

(21) Appl. No.: 13/932,764

(22) Filed: Jul. 1, 2013

(65) Prior Publication Data

US 2015/0002387 A1  Jan. 1, 2015

(51) Int. Cl.
| | |
|---|---|
| G09G 5/00 | (2006.01) |
| G06F 3/01 | (2006.01) |
| H04M 1/725 | (2006.01) |
| H04L 29/06 | (2006.01) |
| H04M 19/04 | (2006.01) |

(52) U.S. Cl.
CPC .............. *G06F 3/014* (2013.01); *G06F 3/017* (2013.01); *H04L 63/0861* (2013.01); *H04M 1/7253* (2013.01); *H04M 1/72519* (2013.01); *H04M 19/04* (2013.01); *H04M 2250/12* (2013.01)

(58) Field of Classification Search
CPC ......... G06F 3/016; G06F 3/011; G06F 3/038; G06F 3/0333; G06F 3/03313
USPC ............. 345/156, 173–179; 178/18.01–18.04
See application file for complete search history.

(56) References Cited

U.S. PATENT DOCUMENTS

| | | | |
|---|---|---|---|
| 7,663,607 | B2 | 2/2010 | Hotelling |
| 7,875,814 | B2 | 1/2011 | Chen |
| 7,920,129 | B2 | 4/2011 | Hotelling |
| 8,031,094 | B2 | 10/2011 | Hotelling |
| 8,031,174 | B2 | 10/2011 | Hamblin |
| 8,040,326 | B2 | 10/2011 | Hotelling |
| 8,049,732 | B2 | 11/2011 | Hotelling |
| 8,179,381 | B2 | 5/2012 | Frey |
| 2009/0315854 | A1 | 12/2009 | Matsuo |
| 2012/0242588 | A1 | 9/2012 | Myers |
| 2012/0242592 | A1 | 9/2012 | Rothkopf |
| 2012/0243151 | A1 | 9/2012 | Lynch |
| 2012/0243719 | A1 | 9/2012 | Franklin |
| 2013/0076612 | A1 | 3/2013 | Myers |
| 2014/0285416 | A1* | 9/2014 | Priyantha et al. ............ 345/156 |

FOREIGN PATENT DOCUMENTS

WO  WO 2012/129247  9/2012

OTHER PUBLICATIONS

U.S. Appl. No. 61/454,936, filed Mar. 21, 2011, Myers.
U.S. Appl. No. 61/454,950, filed Mar. 21, 2011, Lynch.
U.S. Appl. No. 61/454,894, filed Mar. 21, 2011, Rothkopf.

* cited by examiner

*Primary Examiner* — Kimnhung Nguyen
(74) *Attorney, Agent, or Firm* — Baker Botts L.L.P.

(57) ABSTRACT

In one embodiment, an apparatus is provided that includes a ring, a detector, a processor, and a transmitter. The ring is configured to be worn on a finger. The detector, disposed within the ring, is operable to detect a motion associated with the finger. The processor, communicatively coupled to the detector, is operable to determine, based at least upon the motion, that a command should be sent to a mobile device. The transmitter, communicatively coupled to the processor, is operable to communicate the command to the mobile device.

22 Claims, 6 Drawing Sheets

RING ACCESSORY

TECHNICAL FIELD

This disclosure generally relates to wireless communication devices.

BACKGROUND

Mobile devices are becoming more ubiquitous and are being designed to be worn. For example, some mobile devices, such as mobile telephones, are being designed to be worn around a user's limb, such as a wrist or finger. Users can use these wearable mobile devices to make telephone calls, listen to music, retrieve and view information, receive messages such as emails text messages, instant messages, and/or social media messages, and to perform any other appropriate action. Mobile devices include laptop computer, tablet computer, personal digital assistant (PDA), smartphone, satellite navigation device, portable media player, portable game console, kiosk computer, point-of-sale device, or other suitable device.

Some mobile devices may respond to gestures performed by a user. For example, a mobile device may initiate a telephone call if the user brings the mobile device up to the user's ear. In this manner, the mobile devices may receive inputs from the user without the user pushing a hardware or software button of the device.

DESCRIPTION OF EXAMPLE EMBODIMENTS

Figure 1A:
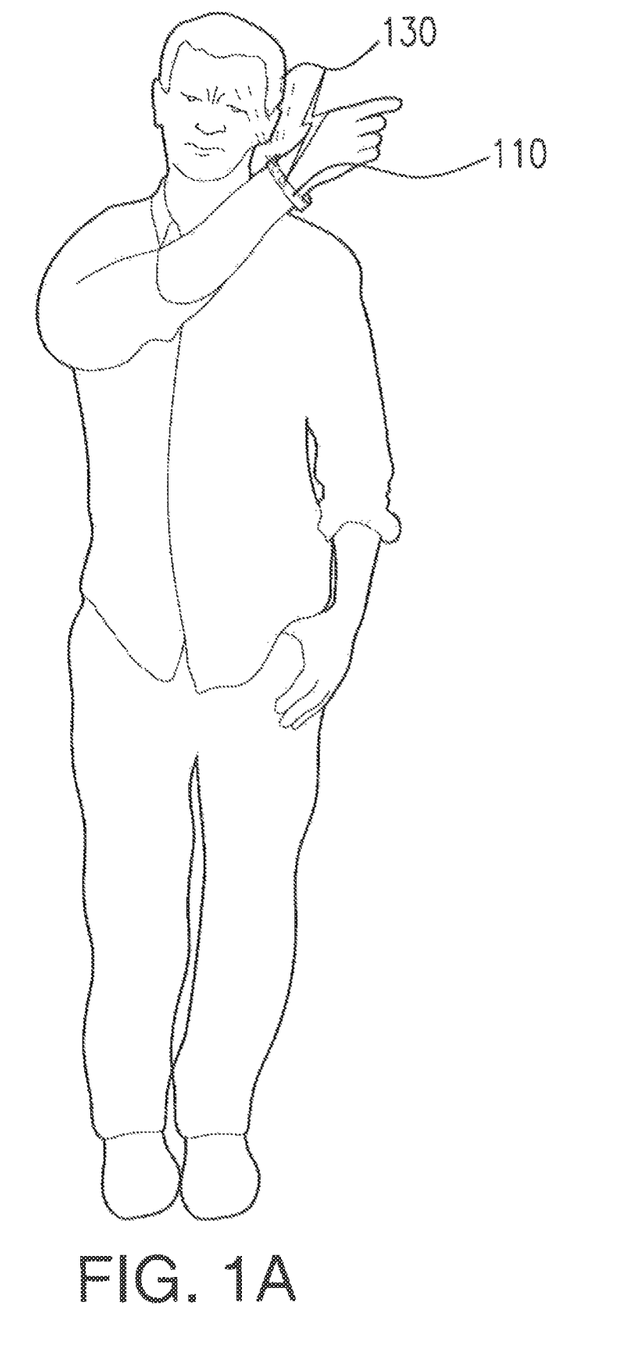
FIG. 1A illustrates a user wearing a mobile device.

Users of mobile devices worn on wrists may experience difficulties with moving and/or gesturing in order to interact with the mobile device on the wrist. FIG. 1A illustrates a user 130 wearing a mobile device 110 around his wrist. As illustrated, user 130 may experience difficulties bringing mobile device 110 up to the user's 130 ear and/or mouth in order to hear and/or speak into mobile device 110 because mobile device 110 is located on user's 130 wrist. Furthermore, mobile device 110 may be unable to detect particular gestures that user 130 makes with his hands. For example, mobile device 110 may be unable to determine that user 130 is pointing at an object or making a hand signal because mobile device 110 is on the user's 130 wrist. As a result, user 130 may be unable to issue particular commands to mobile device 110 using motions and/or gestures.

Figure 1B:
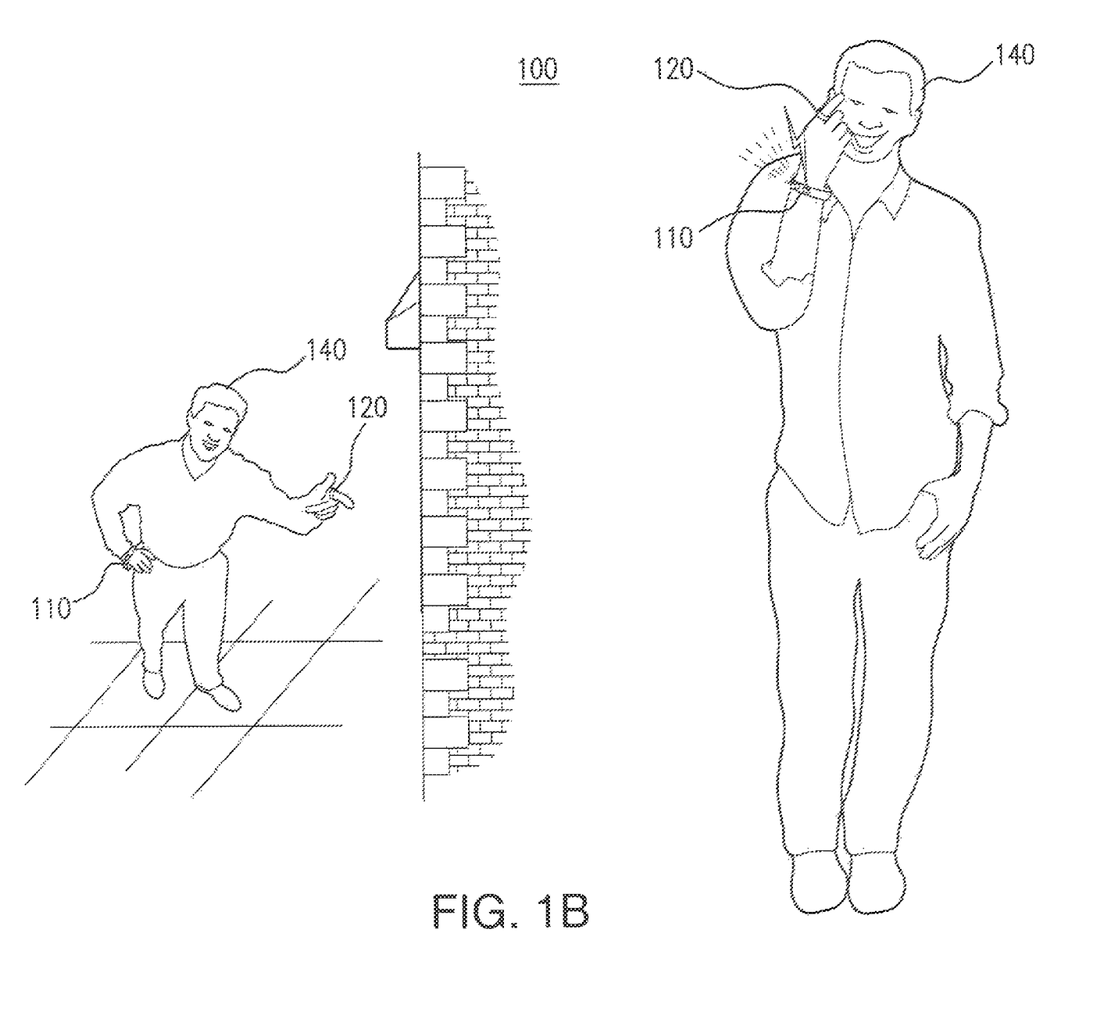
FIG. 1B illustrates a system that includes a user wearing a mobile device and an accessory.

FIG. 1B illustrates a system 100 that includes a user 140 wearing a mobile device 110 and an accessory 120. As illustrated, user 140 may wear mobile device 110 around his wrist and accessory 120 on his finger. User 140 may wear accessory 120 on the same arm and/or finger as device 110 or on the opposite arm and/or finger as mobile device 110. Accessory 120 can communicate with mobile device 110. By using accessory 120, the functionality of mobile device 110 may be expanded and the user experience may be improved.

Accessory 120 may detect when user 140 makes a particular motion and/or gesture with his hand and issue a particular command to mobile device 110 in response to that motion or gesture. For example, user 140 may wear accessory 120 on the opposite arm/finger as mobile device 110 and user his finger on which accessory 120 is worn to point at an object. Accessory 120 may detect that user 140 is pointing at the object and communicate a signal to mobile device 110 in response to that determination. Mobile device 110 may then retrieve information about that object. For example, user 140 may point at a restaurant down the street. The ring accessory 120 may determine that user 140 is pointing at the restaurant and communicate a signal to mobile device 110. Mobile device 110 may then bring up information about that restaurant so that user 140 can determine whether he wants to eat there. As another example, user 140 may point at an object presented on a display or screen. Accessory 120 may determine that user 140 is pointing at the displayed object and communicate a signal to mobile device 110. Mobile device 110 may then retrieve information about that object or execute an application associated with that displayed object.

Accessory 120 may improve the user's 140 experience with mobile device 110. In the example where mobile device 110 is a mobile telephone, user 140 may wear accessory 120 on the same arm and/or finger as mobile device 110. It may be easier for user 140 to bring accessory 120 up to user's 140 ear than to bring mobile device 110 to the ear. When user 140 brings accessory 120 up to user's 140 ear, user 140 may listen to a telephone conversation through accessory 120 while speaking into mobile device 110 on the wrist. By using accessory 120, user 140 may avoid the difficulties of conducting a telephone conversation with mobile device 110 experienced by user 130.

When mobile device 110 receives a message and/or communication, mobile device 110 may signal accessory 120. Accessory 120 may then generate an alert that indicates to user 140 that mobile device 110 received a message and/or communication. For example, mobile device 110 may receive a telephone call, a text message, an email, an instant message, and/or a social media message.

Other functions of the accessory 120 and other interactions between the accessory 120 and mobile device 110 will be described with respect to FIGS. 2 through 4. In general, accessory 120 may be used to communicate with mobile device 110. This communication may improve the user experience and expand the functionality of mobile device 110.

Figure 2A:
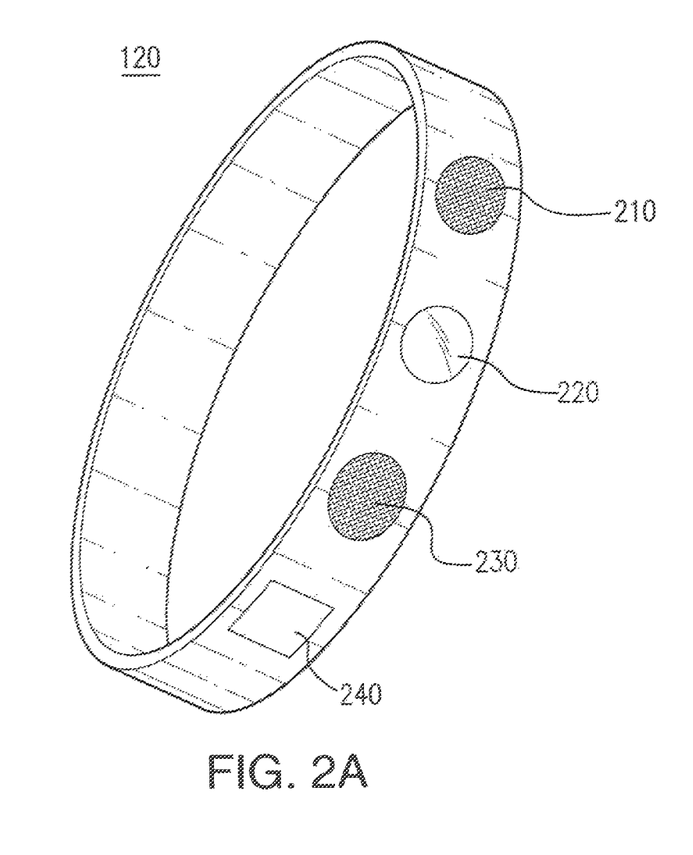
FIG. 2A illustrates an accessory of the system of FIG. 1.
Figure 2B:
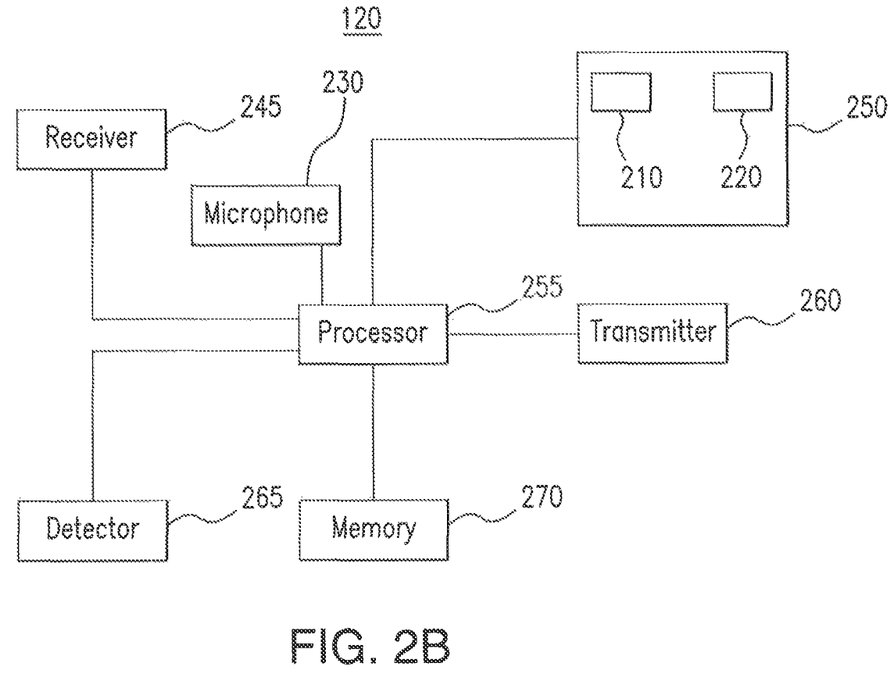
FIG. 2B illustrates an accessory of the system of FIG. 1.

FIGS. 2A and 2B illustrate the accessory 120 of the system 100 of FIG. 1. As seen in FIG. 2A, accessory 120 may be annular and/or configured to be worn on a limb such as, for example, a finger, a toe, an arm, a leg, an ear, and/or any other appropriate limb. This disclosure contemplates accessory 120 being of any appropriate shape. However, discussion of the following embodiments assumes that accessory 120 is a ring configured to be worn around a finger.

As illustrated in FIG. 2A, accessory 120 may include a speaker 210, a light 220, a microphone 230, and an antenna 240. This disclosure contemplates accessory 120 including any appropriate number of speakers 210, lights 220, microphones 230, and/or antennas 240. Accessory 120 may be made of any suitable material such as metal and/or plastic.

Speaker 210 may communicate audible signals to user 140. For example, when mobile device 110 receives a message such as a phone call, email, or text message, mobile device 110 may communicate a signal to accessory 120 indicating that mobile device 110 has received a message. Accessory 120 may determine that an audible signal should be generated to alert the user 140 of the received message. Accessory 120 may generate and/or produce the audible signal through speaker 210. As another example, mobile device 110 may stream sound such as sounds from a telephone call or from a song to accessory 120. In response, accessory 120 may play the sound over speaker 210. This disclosure contemplates speaker 210 being any appropriate sound generating mechanism.

Light 220 may generate a visible signal. For example, light 220 may illuminate, flash, and/or generate an appropriate signal visible to user 140. This disclosure contemplates the visible signal being of any appropriate length and any appropriate color. Light 220 may generate the visible signal in response to a signal from mobile device 110. For example, mobile device 110 may receive a message such as a telephone call, email, or text message and communicate a signal to accessory 120 indicating the receipt of the message. Accessory 120 may receive the signal and instruct light 220 to produce a visible signal in order to indicate to the user 140 that mobile device 110 has received the message. Light 220 may then produce the visible signal such as, for example, by illuminating. When user 140 sees the visible signal from light 220, user 140 will know that mobile device 110 has received a message. Light 220 may be of any appropriate size. For example, light 220 may cover a substantial portion of the surface of accessory 120. In this manner, when light 220 produces the visible signal it may appear to user 140 that accessory 120 has lit up and/or changed color.

Microphone 230 may be used to detect audible signals. For example, user 140 may speak into or around accessory 120. Microphone 230 may detect user's 140 speech and convert the speech into an electric signal understandable by accessory 120 and/or mobile device 110. As another example, user 140 may say "call home." Microphone 230 may detect the statement and accessory 120 may determine based on the detected statement that a command to initiate a telephone call to the user's 140 home telephone number should be communicated. Accessory 120 may then communicate the command to mobile device 110 in order to initiate the telephone call. This disclosure contemplates microphone 230 being any appropriate device that detects audible signals.

Antenna 240 may be used to receive and/or transmit radio frequency signals. For example, antenna 240 may be used to transmit and receive radio frequency signals to and from mobile device 110. This disclosure contemplates accessory 120 having any appropriate number of antennas 240. For example, accessory 120 may have one antenna 240 to transmit signals and another antenna 240 to receive signals.

FIG. 2B illustrates example functional units of the accessory 120 of the system 100 of FIG. 1. As shown in FIG. 2B, accessory 120 may include a receiver 245, a microphone 230, an indicator 250, a processor 255, a transmitter 260, a detector 265, and a memory 270. Receiver 245, microphone 230, indicator 250, transmitter 260, memory 270 and detector 265 may be communicatively coupled to processor 255. Some or all of these units may be disposed within and/or coupled to a casing and/or housing of accessory 120. For example, as illustrated in FIG. 2B, microphone 230 may be coupled to the annular casing of accessory 120. This disclosure contemplates receiver 245, microphone 230, indicator 250, processor 255, transmitter 260, detector 265, and/or memory 270 performing any of the functions described herein as being performed by accessory 120.

Memory 270 may be used to store instructions and/or data associated with the operation of accessory 120. For example, memory 270 may store instructions executable by processor 255 for the operation of accessory 120. As another example, memory 270 may store information associated with user 140 used in the operation of accessory 120. Memory 134 may store, either permanently or temporarily, data, operational software, or other information for processor 132. Memory 134 may include any one or a combination of volatile or non-volatile local or remote devices suitable for storing information. For example, memory 134 may include random access memory (RAM), read only memory (ROM), magnetic storage devices, optical storage devices, or any other suitable information storage device or a combination of these devices.

Processor 255 may be used to perform the logic and/or determination functions of accessory 120. For example, processor 255 may determine whether indicator 250 should produce a signal in response to a signal received by receiver 245. As another example, processor 255 may determine whether transmitter 260 should transmit a signal in response to an audible signal detected by microphone 230. Processor 132 may include any hardware and/or software that operates to control and process information. Processor 132 may be a programmable logic device, a microcontroller, a microprocessor, any suitable processing device, or any suitable combination of the preceding.

Receiver 245 may be used to receive radio frequency signals. For example, receiver 245 may receive radio frequency signals from mobile unit 110. Receiver 245 may convert the received radio frequency signals into electric signals understandable by processor 255. Accessory 120 may then perform an action in response to the received signal. This disclosure contemplates receiver 245 being any appropriate mechanism that may receive radio frequency signals such as, for example, antenna 240.

Transmitter 260 may be used to transmit radio frequency signals from accessory 120. Transmitter 260 may receive signals from processor 255, convert the signals into radio frequency signals, and transmit the radio frequency signals to mobile device 110. This disclosure contemplates transmitter 260 being any appropriate mechanism to transmit radio frequency signals from accessory 120 such as, for example, antenna 240.

This disclosure contemplates accessory 120 including a transceiver unit comprising both receiver 245 and transmitter 260. Accessory 120 may further include circuitry and/or switches that control the transceiver unit to switch between receive and transmit modes.

Detector 265 may be used to detect properties associated with user 140 and/or his environment. After making a detection, detector 265 may communicate the detection to processor 255. This disclosure contemplates processor 255 responding to the detection in any appropriate manner. This disclosure further contemplates detector 265 including any number of mechanisms to make any appropriate detection.

Detector 265 may include a motion detector such as an accelerometer that detects movement of accessory 120 and/or user 140. After detecting the movement, detector 265 may communicate a signal to processor 255 indicating that the movement was detected. Processor 255 may then determine the appropriate response to the detected motion. For example, the detected motion may correspond to a command being issued to mobile device 110. In response to detecting the motion, processor 255 may issue the command and transmitter 260 may transmit the command to mobile device 110. For example, detector 265 may determine that user 112 has brought accessory 120 close to his ear. Detector 265 may communicate a signal to processor 255 indicating that accessory 120 has been moved close to the user's 140 ear. Processor 255 may determine that moving accessory 120 close to one's ear corresponds to a command of initiating a phone call. In response, processor 255 may issue a command to initiate a phone call to transmitter 260, and transmitter 260 may communicate that command to mobile device 110. In response, mobile device 110 may initiate a telephone call.

Detector 265 may include a biometric detector such as, for example, a pulse detector, a blood oxygen level detector, a heart rate detector, and/or a blood pressure detector. The biometric detector may communicate to processor 255 signals indicating the biometric information detected by the biometric detector. For example, a heart rate detector may detect that the heart rate associated with user 140 is a hundred beats per minute. The heart rate detector may communicate a signal to processor 255 indicating the heart rate associated with user 140. Processor 255 may then compare the detected heart rate with a stored threshold heart rate. If the detected heart rate exceeds the threshold, processor 255 may communicate a signal to transmitter 260 indicating that the heart rate of user 140 has exceeded the threshold. Transmitter 260 may then transmit the signal to mobile device 110 and mobile device 110 may alert user 140 that his heart rate has exceeded the threshold. This disclosure contemplates the detector 265 detecting any appropriate type of biometric information and accessory 120 and mobile device 110 taking any appropriate action in response to the detected biometric information.

Detector 265 may include a position detector that may detect the position, location, and/or direction of accessory 120. The position detector may report a detected position, location, and/or direction to processor 255, and processor 255 may determine an appropriate response to the detected position, location, and/or direction. For example, the position detector may detect that accessory 120 is in a particular location and pointing in a particular direction. The position detector may communicate the particular location and direction to processor 255. Processor 255 may determine, based on the particular location and direction, that user 140 is pointing at a particular restaurant. Processor 255 may then communicate a signal to transmitter 260 indicating that information associated with the restaurant should be provided to user 140. Transmitter 260 may then transmit the signal to mobile unit 110, and mobile unit 110 may respond by retrieving information associated with the restaurant. As another example, processor 255 may determine that user 140 is pointing at a particular object presented on a display or screen. Processor 255 may then communicate a signal to transmitter 260 indicating that information about the displayed object should be retrieved and/or that an application associated with the displayed object should be executed. Transmitter 260 may then transmit the signal to mobile unit 110, and mobile unit 110 may respond by retrieving information about the displayed object and/or executing the application. In an alternative embodiment, upon receiving the particular location and direction, processor 255 may communicate a signal to transmitter 260 indicating that user 140 is pointing at an object described by the particular location and direction. Transmitter 260 may then transmit the particular location and direction to mobile device 110 and mobile device 110 may respond by determining the object to which user 140 is pointing and retrieving information associated with that object. This disclosure contemplates the position detector determining any appropriate position, location, and/or direction and accessory 120 and mobile device 110 performing any appropriate action in response to a detected position, location, and/or direction.

Position detector may further determine the distance between accessory 120 and mobile device 110. The position detector may report the distance to the mobile device to processor 255, and processor 255 may determine based on that distance that a particular command should be communicated to mobile device 110. Processor 255 may then communicate a signal indicating that command to transmitter 260. Transmitter 260 may then transmit the signal to mobile device 110 in order to issue the command. For example, processor 255 may determine based on the distance between accessory 120 and mobile device that a command to initiate a telephone call should be issued. Processor 255 may then communicate to transmitter 260, a signal indicating the command to initiate the telephone call. Transmitter 260 may then transmit the signal to mobile device 110, and mobile device 110 may initiate the phone call. This disclosure contemplates accessory 120 and mobile device 110 performing any appropriate action in response to any detected distance between accessory 120 and mobile device 110.

Detector 265 may include mechanical switches such as buttons and/or touch sensor switches. When detector 265 detects that user 140 has actuated a mechanical switch such as, for example, pressing a button and/or touched a touch sensor switch, detector 265 may communicate a signal to processor 255 indicating that a mechanical switch and/or a touch sensor switch has been actuated and/or touched. Processor 255 may then communicate the signal to transmitter 260 to be transmitted to mobile device 110, and/or determine a corresponding command to be communicated to mobile device 110 via transmitter 260. For example, accessory 120 may include a touch sensor. When user 140 touches the touch sensor, detector 265 may determine that user 140 has touched the touch sensor. Detector 265 may then communicate a signal to processor 255 indicating that user 140 has touched the touch sensor. Processor 255 may determine that the touch on the touch sensor corresponds to a command to redial a number. Processor 255 may then communicate a signal to transmitter 260 instructing transmitter 260 to communicate the command to mobile device 110. After transmitter 260 transmits the command to mobile device 110, mobile device 110 may redial the telephone number. This disclosure contemplates accessory 120 and/or mobile device 110 taking any appropriate action in response to user 140 actuating a mechanical switch and/or touching a touch sensor.

Indicator 250 may be used to communicate an alert to user 140. Indicator 250 may include light 220 and speaker 210 illustrated in FIG. 2B. Indicator 250 may also include a motor that when active causes accessory 120 to vibrate. By using the motor, accessory 120 can alert user 140 by generating a vibration. This disclosure contemplates indicator 250 generating any appropriate type of alert in response to any appropriate condition such as, for example, mobile device 110 receiving a telephone call, an email, a text message, an instant message, and/or a social media message.

In operation, accessory 120 may be used to communicate with mobile device 110. In particular instances, accessory 120 may respond to communications from mobile device 110, and in some instances mobile device 110 may respond to communications from accessory 120. Accessory 120 may communicate commands for a mobile device 110 to perform particular actions. Mobile device 110 may communicate signals indicating that accessory 120 should alert user 140 of a particular event.

Mobile device 110 may communicate signals to accessory 120 indicating that accessory 120 should alert user 140 that a particular event has occurred. For example, mobile device 110 may receive a message such as, for example, a telephone call, an email, a text message, an instant message, and/or a social media message. Mobile device 110 may determine that user 140 should be alerted of the receipt of the message. Mobile device 110 may then communicate a signal to accessory 120 indicating that an alert should be generated. Upon receiving the signal, accessory 120 may generate the appropriate alert. This disclosure contemplates accessory 120 generating any appropriate alert to any appropriate event. For example, accessory 120 may generate an audible signal through speaker 210 indicating that mobile device 110 has received a telephone call. As another example, accessory 120 may generate a visible signal of a particular color to indicate that a detected blood pressure of user 140 has exceeded a threshold.

Accessory 120 may generate an alert in response to a signal from mobile device 110. This disclosure contemplates accessory generating any appropriate type of alert in response to any appropriate signal from mobile device 110. For example, accessory 120 may generate an audible alert through speaker 210. As another example, accessory 120 may generate a vibration. As yet another example, accessory 120 may generate a visible signal such as illuminating or flashing a light and/or changing the color of a light.

Accessory 120 may detect motion associated with accessory 120 and/or user 140. For example, user 140 may move accessory 140 next to his ear. Accessory 120 may detect this motion and communicate a signal to mobile device 110 indicating that the user has moved accessory 120 to his ear. Mobile device 110 may then determine an appropriate response to the detected motion such as, for example, initiating a telephone call. In particular embodiments, accessory 120 may determine that a command should be communicated to mobile device 110 in response to detecting the motion. For example, accessory 120 may detect that user 140 has moved accessory 120 to his ear. Accessory 120 may determine that a telephone call should be initiated based on that detected motion. Accessory 120 may then communicate a command to initiate a telephone call to mobile device 110 and mobile device 110 may initiate the telephone call. As another example, mobile device 110 may have received a telephone call and indicated to accessory 120 that an alert should be generated. After accessory 120 generates the alert, user 140 may move accessory 120 up to his ear. Accessory 120 may detect that motion and determine that the call should be answered in response to that motion. Accessory 120 may then communicate a command to mobile device 110 to answer the call.

Accessory 120 may detect the position, location, and/or direction of accessory 120 and/or user 140. For example, if user 140 is wearing accessory 120 on his finger and points that finger at an object such as a restaurant, accessory 120 may detect its location and the direction to which it is pointing. In particular embodiments, accessory 120 may communicate the determined location and direction to mobile device 110. In response, mobile device 110 may use the determined location and direction to determine the object at which user 140 is pointing. In this example, mobile device 110 may determine that user 140 is pointing at the restaurant. Mobile device 110 may then retrieve information about the restaurant in order to help user 140 determine if he wants to eat there. In other embodiments, accessory 120 may determine the object at which user 140 is pointing and communicate to mobile device 110 a name or ID associated with the object. Mobile device 110 may then retrieve information about that object for user 140. This disclosure contemplates accessory 120 and mobile device 110 performing any appropriate action in response to a determined position, location, and/or direction.

Accessory 120 may detect an audible signal through a mechanism such as microphone 230, for example. Accessory 120 may then take any appropriate action in response to receiving the audible signal. For example, user 140 may speak into microphone 230 a command that indicates a telephone call should be placed. In response, accessory 120 may transmit a signal corresponding to the audible command issued by user 140 to mobile device 110. Mobile device 110 may then initiate the telephone call in response to the command. As another example, user 140 may say the phrase "call home" into microphone 230. Accessory 120 may convert the audible signal into an electric signal and/or a radio frequency signal. Accessory 120 may then communicate the signal to mobile device 110 and mobile device 110 may initiate a telephone call to the home of the user 140. This disclosure contemplates accessory 120 and mobile device performing any appropriate type of action in response to a detected audible signal.

Accessory 120 may detect biometric information associated with user 140. For example, accessory 120 may detect a pulse, a blood oxygen level, a heart rate and/or a blood pressure associated with user 140. Accessory 120 and/or mobile device 110 may compare the detected biometric information with thresholds and may generate an alert if a threshold is exceeded. For example, accessory 120 may determine that user's 140 blood pressure is at a particular level. Accessory 120 may communicate user's 140 blood pressure to mobile device 110. Mobile device 110 may determine that the blood pressure has exceeded a threshold and communicate a signal to accessory 120 indicating that an alert should be generated. Accessory 120 may then generate the appropriate alert. As another example, accessory 120 may determine that user's 140 heart rate is at a particular level. Accessory 120 may also determine that user's 140 heart rate has exceeded a threshold and generate an appropriate alert in response to that determination. In this manner, user 140 may be alerted to his health condition. This disclosure contemplates accessory 120 detecting any appropriate type of biometric information and accessory 120 and mobile device 110 generating any appropriate type of alert in response to the detected biometric information.

In particular embodiments, user 140 may use accessory 120 to authenticate himself. For example, user 120 may perform a particular motion or gesture corresponding to particular authentication parameters, such as usernames, passwords, personal identification numbers, and/or signatures. Accessory 120 may detect the motion and/or gesture. Then accessory 120 and/or mobile device 110 may determine that the gesture corresponds to a particular username, password, personal identification number, and/or signature and authenticate user 140. As an example, the appropriate username and password to user's 140 email account may correspond to user 140 touching his thumb and middle finger together. When user 140 puts his thumb on his middle finger, accessory 120 may detect that that particular gesture has occurred. Accessory 120 and/or mobile device 110 may then determine that the detected gesture corresponds to the user's 140 username and password. Mobile device 110 may then authenticate user 140 so that he may access his email. This disclosure contemplates accessory 120 and/or mobile device 110 performing any appropriate type of authentication in response to any appropriate type of motion or gesture.

Accessory 120 may further detect a touch by user 140 and mobile device 110 and/or accessory 120 may perform a particular action in response to that touch. For example, user 140 may a touch a touch sensor on accessory 120 to indicate that a received telephone call should be answered. Accessory 120 may detect the touch on the touch sensor and in response may communicate a command to answer the telephone call and/or a signal indicating that a touch has been detected to mobile device 110. Mobile device 110 may then answer the telephone call. This disclosure contemplates mobile device 110 and accessory 120 performing any appropriate action in response to detecting a touch.

Figure 3:
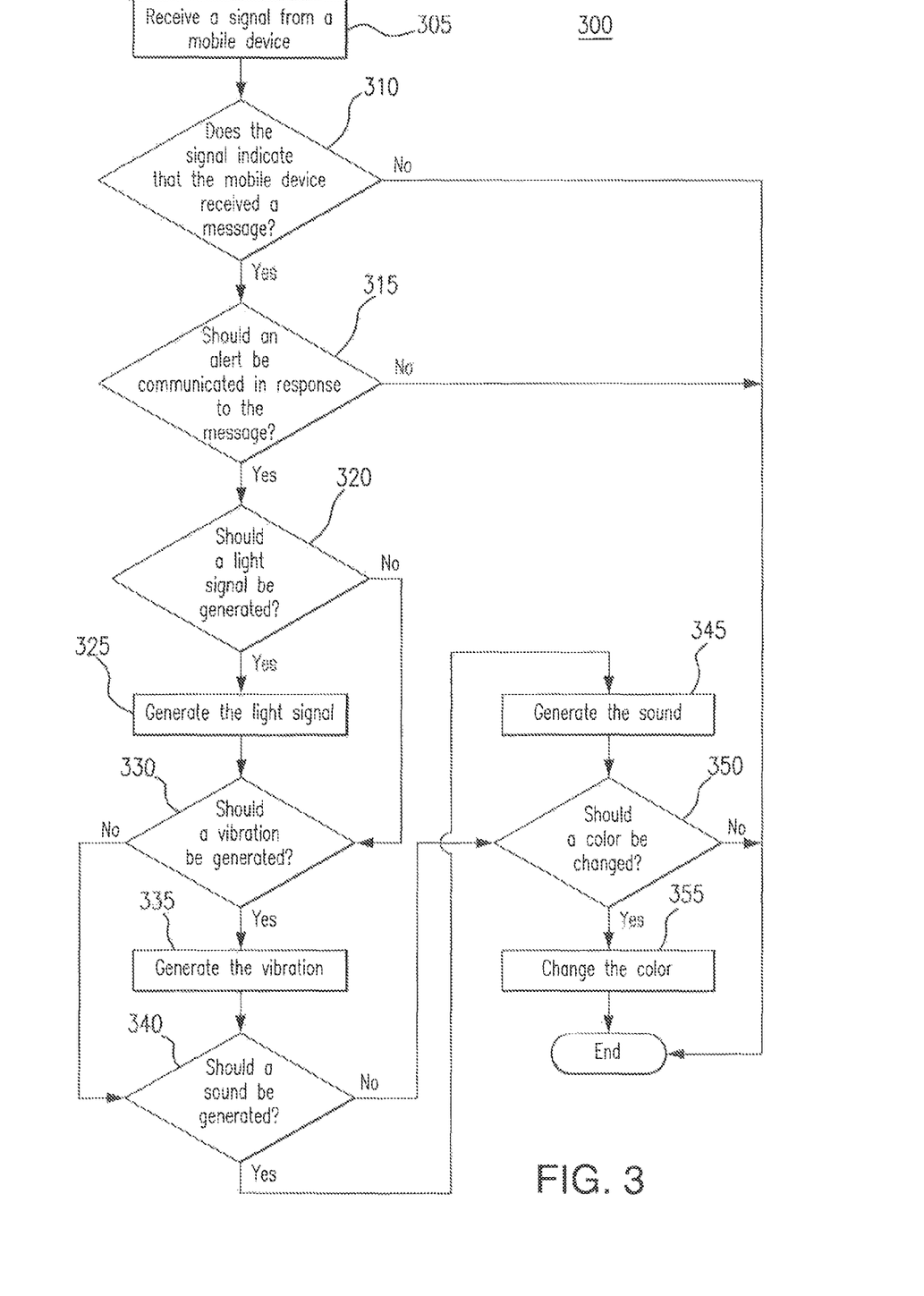
FIG. 3 is a flowchart illustrating a method of alerting a user using the system of FIG. 1.

FIG. 3 is a flowchart illustrating a method 300 of alerting a user using the system 100 of FIG. 1. Accessory 120 may perform method 300. In particular embodiments, accessory 120 and mobile device 110 may appropriately notify user 140 of a received message by performing method 300. For example, accessory 120 may notify or alert user 140 of a received telephone call, email message, text message, instant message, and/or social media message.

In step 305, accessory 120 may receive a signal from a mobile device. Accessory 120 may then determine whether the signal indicates that the mobile device received a message in step 310. For example, accessory 120 may determine whether the mobile device received a telephone call, email, text message, instant message, and/or social media message. If the mobile device did not receive a message, then accessory 120 may conclude.

If the mobile device received a message, then accessory 120 may determine whether an alert should be communicated in response to the message in step 315. The alert may indicate to user 140 that the mobile device has received a message. In particular embodiments, accessory 120 may make this determination based on instructions or tables stored in memory. If no alert is to be communicated, accessory 120 may conclude.

If accessory 120 determines that an alert should be communicated, accessory 120 may determine whether a light signal should be generated in step 320. If accessory 120 determines that a light signal should be generated, accessory 120 may generate the light signal in step 325. In particular embodiments, accessory 120 may generate the light signal by illuminating and/or flashing a light. User 140 may see the generated light signal and be alerted that the mobile device has received a message. After generating the light signal, or if accessory 120 determines that no light signal should be generated, accessory 120 may determine whether a vibration should be generated in step 330.

If accessory 120 determines that a vibration should be generated, accessory 120 may generate the vibration in step 335. In particular embodiments, accessory 120 may activate a motor to generate the vibration. User 140 may feel the vibration and be alerted that the mobile device has received a message. After generating the vibration or if accessory 120 determines that no vibration should be generated, accessory 120 may determine whether a sound should be generated in step 340.

If accessory 120 determines that a sound should be generated, accessory 120 may generate the sound in step 245. In particular embodiments, accessory 120 may generate the sound and produce it over speaker 210. User 140 may hear the generated sound and be alerted that the mobile device has received a message. After generating the sound, or if accessory 120 determines that no sound should be generated, accessory 120 may determine whether a color should be changed in step 350.

If accessory 120 determines that a color should be changed, accessory 120 may change its color in step 355. In particular embodiments, accessory 120 may change its color by changing the color of a light on accessory 120. User 140 may see the changed color of accessory 120 and be alerted that the mobile device has received a message. After changing the color, or if accessory 120 determines that no color should be changed, accessory 120 may conclude.

Figure 4:
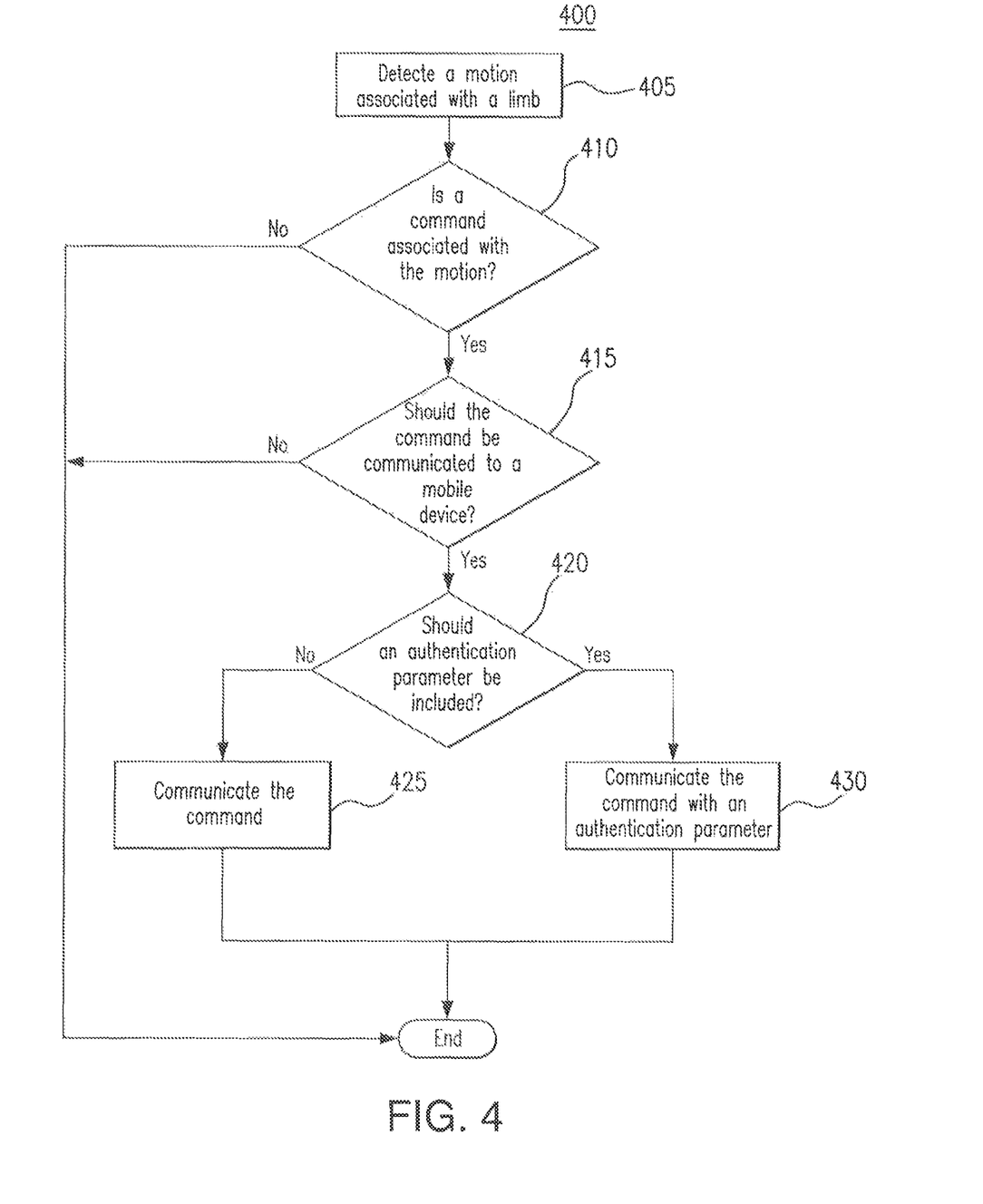
FIG. 4 is a flowchart illustrating a method of communicating a command using the system of FIG. 1.

FIG. 4 is a flowchart illustrating a method 400 of communicating a command using the system 100 of FIG. 1. Accessory 120 may perform method 500. In step 405, accessory 120 may detect a motion associated with a limb. For example, accessory 120 may detect that user 140 has moved accessory 120 to user's 140 ear. As another example, accessory 120 may determine a position, location, and/or direction associated with accessory 120.

Accessory 120 may then determine whether a command is associated with the detected motion in step 410. For example, accessory 120 may determine that moving accessory 120 to user's 140 ear corresponds to a command to initiate a telephone call. As another example, accessory 120 may determine that a hand motion or gesture corresponds to a command to access email. If no command is associated with the motion, accessory 120 may conclude. If accessory 120 determines that a command is associated with a detected motion, accessory 120 may continue to determine whether the command should be communicated to a mobile device at step 415. If the command should not be communicated to the mobile device, accessory 120 may conclude.

If accessory 120 determines that the command should be communicated to the mobile device, accessory 120 may determine whether an authentication parameter such as a username and/or password should be included in the communication to the mobile device in step 420. In particular embodiments, accessory 120 may make this determination based on instructions and/or information stored in memory. If accessory 120 determines that an authentication parameter should not be included, accessory 120 may communicate the command in step 425. If accessory 120 determines that the authentication parameter should be included, accessory 120 may communicate the command with the authentication parameter in step 430.

As an example, accessory 120 may determine that user 140 has placed his thumb on his middle finger. Accessory 120 may detect this motion and determine that this motion corresponds to a command to access the user's 140 email. Accessory 120 may further determine that the motion of placing the thumb on the middle finger corresponds to the user's 140 username and password. In response, accessory 120 may communicate the command to access the user's 140 email along with the user's 140 username and password. When mobile device 110 receives the command, the username and the password, mobile device 110 may authenticate user 140 and access his email.

Although the present disclosure includes several embodiments, a myriad of changes, variations, alterations, transformations, and modifications may be suggested to one skilled in the art, and it is intended that the present disclosure encompass such changes, variations, alterations, transformations, and modifications as fall within the scope of the appended claims.

What is claimed is:

1. An apparatus comprising:
a ring configured to be worn on a finger;
a detector disposed within the ring and operable to detect a motion associated with the finger;
a processor communicatively coupled to the detector and operable to determine, based at least upon the motion, that a command should be sent to a mobile device; and
a transmitter communicatively coupled to the processor and operable to communicate the command to the mobile device.

2. The apparatus of claim 1, wherein:
the mobile device is configured to be worn by a person having the finger and the motion associated with the finger is a motion of the finger.

3. The apparatus of claim 1, wherein the motion indicates at least one of a username, a password, a personal identification number, and a signature.

4. The apparatus of claim 1, wherein:
the processor is further operable to determine, based at least in part upon the motion, that the finger is pointing at an object; and
the command indicates that information associated with the object should be determined.

5. The apparatus of claim 1, wherein the command indicates at least one of that a telephone call should be answered and that a telephone call should be placed.

6. The apparatus of claim 1, further comprising a touch sensor operable to detect a touch on the ring, wherein the processor is further operable to determine, based at least upon the touch, that a second command should be communicated to the mobile device.

7. The apparatus of claim 1, wherein:
the detector is further operable to detect a location associated with the apparatus; and
the processor is further operable to determine, based at least in part upon the location, that a second command should be communicated to the mobile device.

8. The apparatus of claim 1, wherein the mobile device is configured to be worn around a wrist.

9. A system comprising:
a mobile device element configured to be worn around a wrist; and
a ring element configured to be worn on a limb, the ring element comprising:
a detector disposed within the ring and operable to detect a motion associated with the limb;
a processor communicatively coupled to the detector and operable to determine, based at least upon the motion, that a command should be sent to a mobile device; and
a transmitter communicatively coupled to the processor and operable to communicate the command to the mobile device.

10. The system of claim 9, wherein:
the detector is further operable to detect at least one of a pulse, a blood oxygen level, a heart rate, and a blood pressure, and
the transmitter is further operable to communicate a second command to the mobile device if at least one of the pulse, the blood oxygen level, the heart rate, and the blood pressure exceed a threshold.

11. The system of claim 9, wherein the motion indicates at least one of a username and a password.

12. The system of claim 9, wherein:
the limb is a finger;
the processor is further operable to determine, based at least in part upon the motion, that the finger is pointing at an object; and
the command indicates that information associated with the object should be determined.

13. The system of claim 9, wherein the command indicates at least one of that a telephone call should be answered and that a telephone call should be placed.

14. The system of claim 9, further comprising a touch sensor operable to detect a touch on the ring, wherein the processor is further operable to determine, based at least upon the touch, that a second command should be communicated to the mobile device.

15. The system of claim 9, wherein:
the detector is further operable to detect a location relative to the mobile device; and
the processor is further operable to determine, based at least in part upon the location, that a second command should be communicated to the mobile device.

16. A method comprising:
wearing a ring on a finger;
detecting, by a detector disposed within the ring, a motion associated with the finger;
determining, by a processor communicatively coupled to the detector, based at least upon the motion, that a command should be sent to a mobile device worn around a wrist; and
communicating, by a transmitter communicatively coupled to the processor, the command to the mobile device.

17. The method of claim 16, further comprising:
detecting, by the detector, at least one of a pulse, a blood oxygen level, a heart rate, and a blood pressure, and
communicating, by the transmitter, a second command to the mobile device if at least one of the pulse, the blood oxygen level, the heart rate, and the blood pressure exceed a threshold.

18. The method of claim 16, wherein the motion indicates at least one of a username and a password.

19. The method of claim 16, further comprising:
determining, by the processor, based at least in part upon the motion, that the finger is pointing at an object;
wherein the command indicates that information associated with the object should be determined.

20. The method of claim 16, wherein the command indicates at least one of that a telephone call should be answered and that a telephone call should be placed.

21. The method of claim 16, further comprising:
detecting, by a touch sensor, a touch on the ring; and
determining, by the processor, based at least upon the touch, that a second command should be communicated to the mobile device.

22. The method of claim 16, further comprising:
detecting, by the detector, a location relative to the mobile device; and
determining, by the processor, based at least in part upon the location, that a second command should be communicated to the mobile device.

* * * * *